(12) United States Patent
Pellegrini et al.

(10) Patent No.: US 6,461,038 B2
(45) Date of Patent: Oct. 8, 2002

(54) DENTAL X-RAY SENSOR HOLDER

(76) Inventors: Richard R. Pellegrini, 801 N. Larkin Ave., Suite 105, Joliet, IL (US) 60435; Anthony J. Pavnica, 1813 Briar Cliff, New Lenox, IL (US) 60451

( * ) Notice: Subject to any disclaimer, the term of this patent is extended or adjusted under 35 U.S.C. 154(b) by 0 days.

(21) Appl. No.: 09/739,855

(22) Filed: Dec. 18, 2000

(65) Prior Publication Data

US 2002/0076001 A1 Jun. 20, 2002

(51) Int. Cl.$^7$ ............................. A61B 6/14; G03B 42/04
(52) U.S. Cl. ...................... 378/191; 378/98.8; 378/168; 378/169
(58) Field of Search ................................ 378/168, 169, 378/170, 172, 173, 177, 191, 184, 187, 98.8, 98.2

(56) References Cited

U.S. PATENT DOCUMENTS

| | | | |
|---|---|---|---|
| D246,798 S | 12/1977 | Jermyn | D24/2 |
| 4,075,494 A | 2/1978 | Jermyn | 378/170 |
| D254,805 S | 4/1980 | Edeland | D24/2 |
| 4,361,974 A | 12/1982 | Wood | 40/701 |
| 4,626,216 A | 12/1986 | Strong-Grainger | 378/168 |
| 4,815,117 A | 3/1989 | Waldo | 378/168 |
| 4,866,750 A | 9/1989 | Chavarria et al. | 378/168 |
| 5,001,738 A | 3/1991 | Brooks | 378/170 |
| 5,256,982 A | 10/1993 | Willis | 378/168 |
| 5,274,691 A | * 12/1993 | Neri | 378/168 |
| 5,289,522 A | * 2/1994 | Kanbar et al. | 378/168 |
| 5,677,537 A | * 10/1997 | Pfeiffer | 378/191 |
| 5,737,388 A | 4/1998 | Kossila | 378/168 |
| 5,784,433 A | * 7/1998 | Higa | 378/168 |

OTHER PUBLICATIONS

Dentsply RINN (2000); Product Catalog 2000–2001, pp. 1–36.
IDS '99 Press Release "Dürr Vistaray Digital Intraoral X–Ray" (2 pages).
Sens–A–Ray 2000 Intraoral Digital X–Ray (4 pages).
Dentsply RINN (1997); Uni–Bite (1 page).
Dentsply RINN (1997); Tech Info on Uni–Bite Film Holder (1 page).
Dentsply RINN (1997); Tech Info on Endoray II Film Holder (1 page).
Dentsply RINN (1997); Disposables (2 pages).
Schick Technologies, Inc., CDR™ Computed Dental Radiography (1 page), No Date.
Digital X–Rays, Georgetown Family Dentistry (1 page), No Date.
Provision Dental Systems, Inc. (1998); Accessories (1 page).
DMD Dental/Medical Diagnostic Systems, Inc. (1996–2000); World's Thinnest Sensors (1 page).
ScanLogic Corporation (1999); Computed Dental Radiography (CDR) and DDRCam (1 page).

* cited by examiner

Primary Examiner—Drew A. Dunn
(74) Attorney, Agent, or Firm—Marshall, Gerstein & Borun

(57) ABSTRACT

A holder for a dental X-ray image sensor is provided which enables adjustment of the position of the sensor after placement of the holder and sensor in the mouth. A flexible, deformable or elastic loop holds the sensor in place but enables manipulation of the sensor position. The elastic loop is connected to a handle member. A slot also is provided in the handle for accommodating wire leads connected to the sensor.

12 Claims, 7 Drawing Sheets

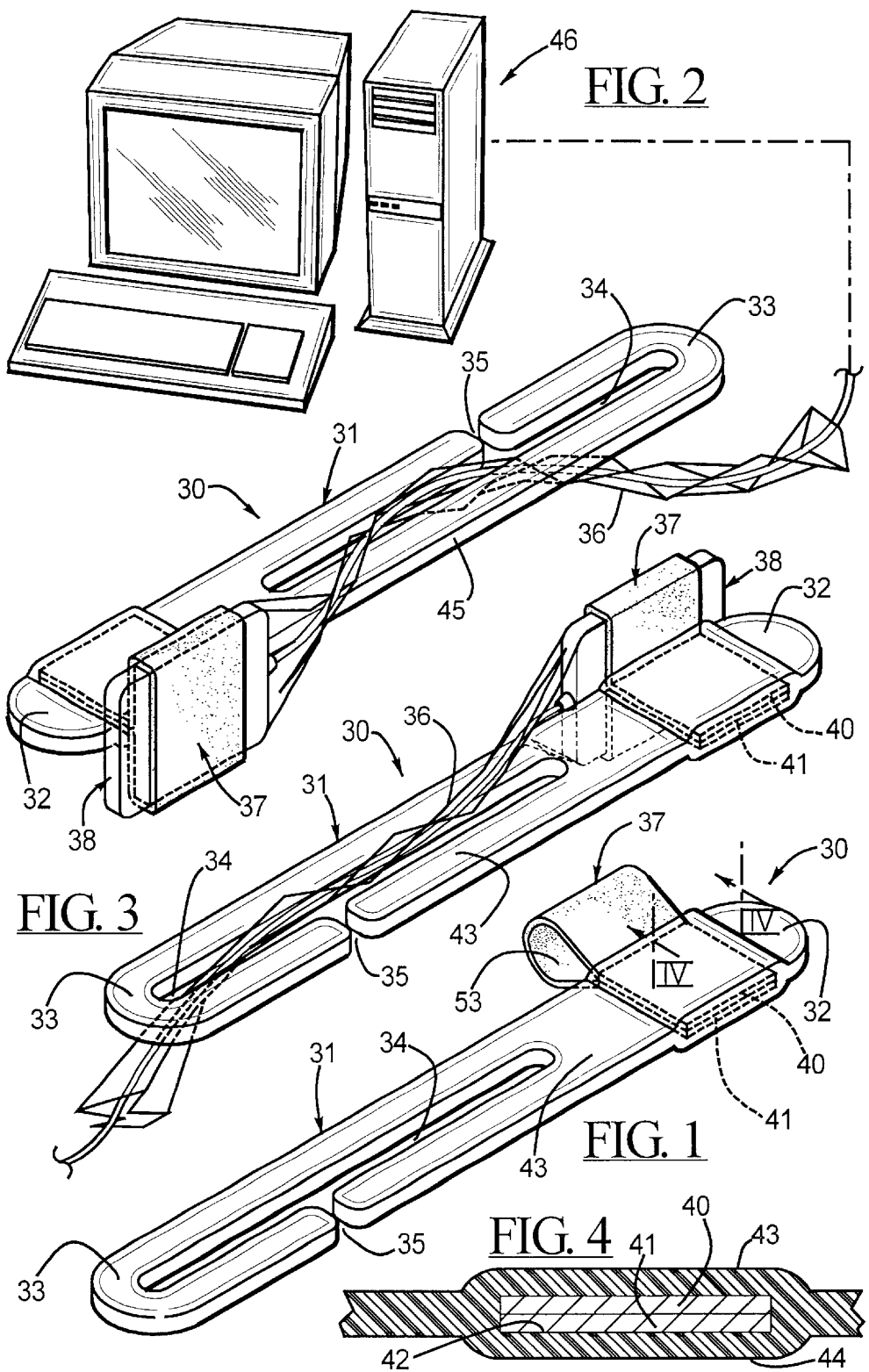

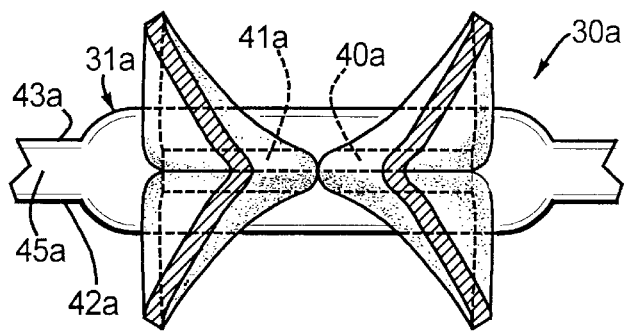
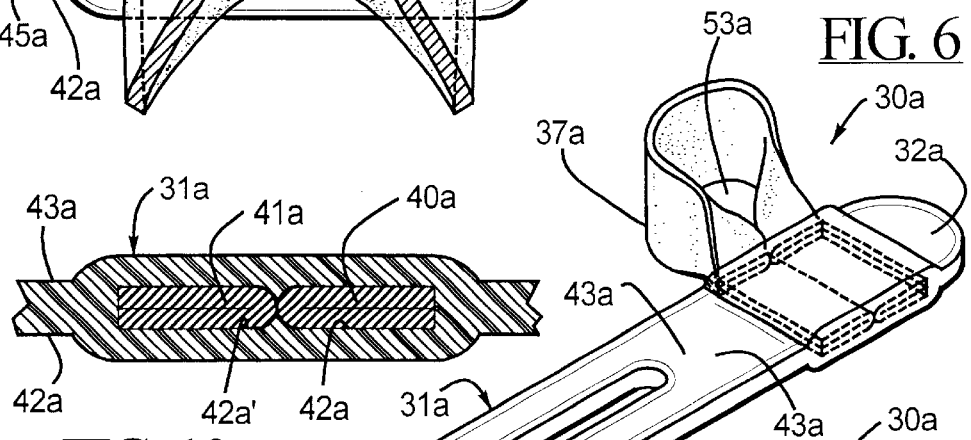
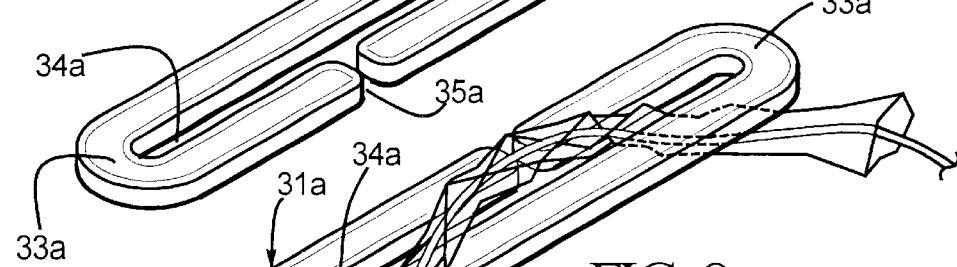
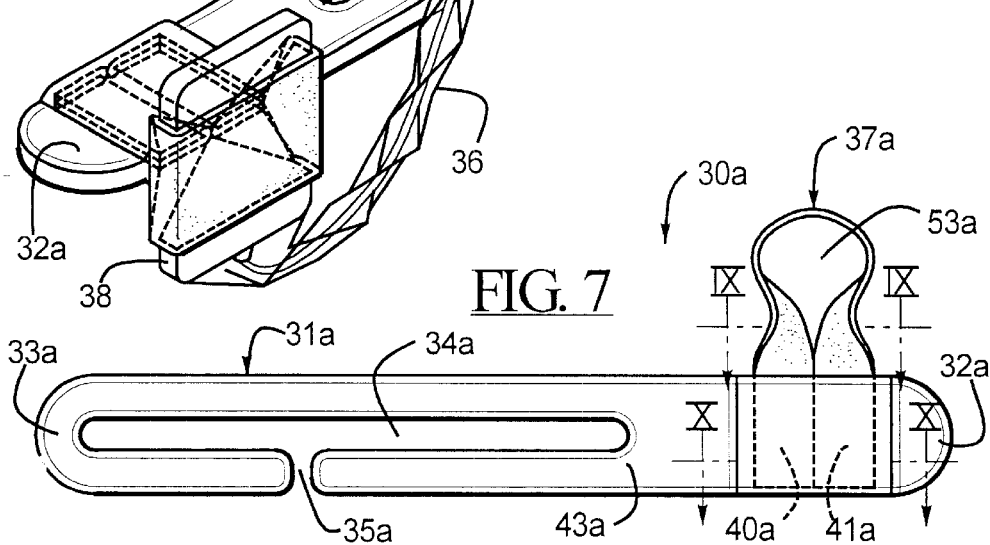

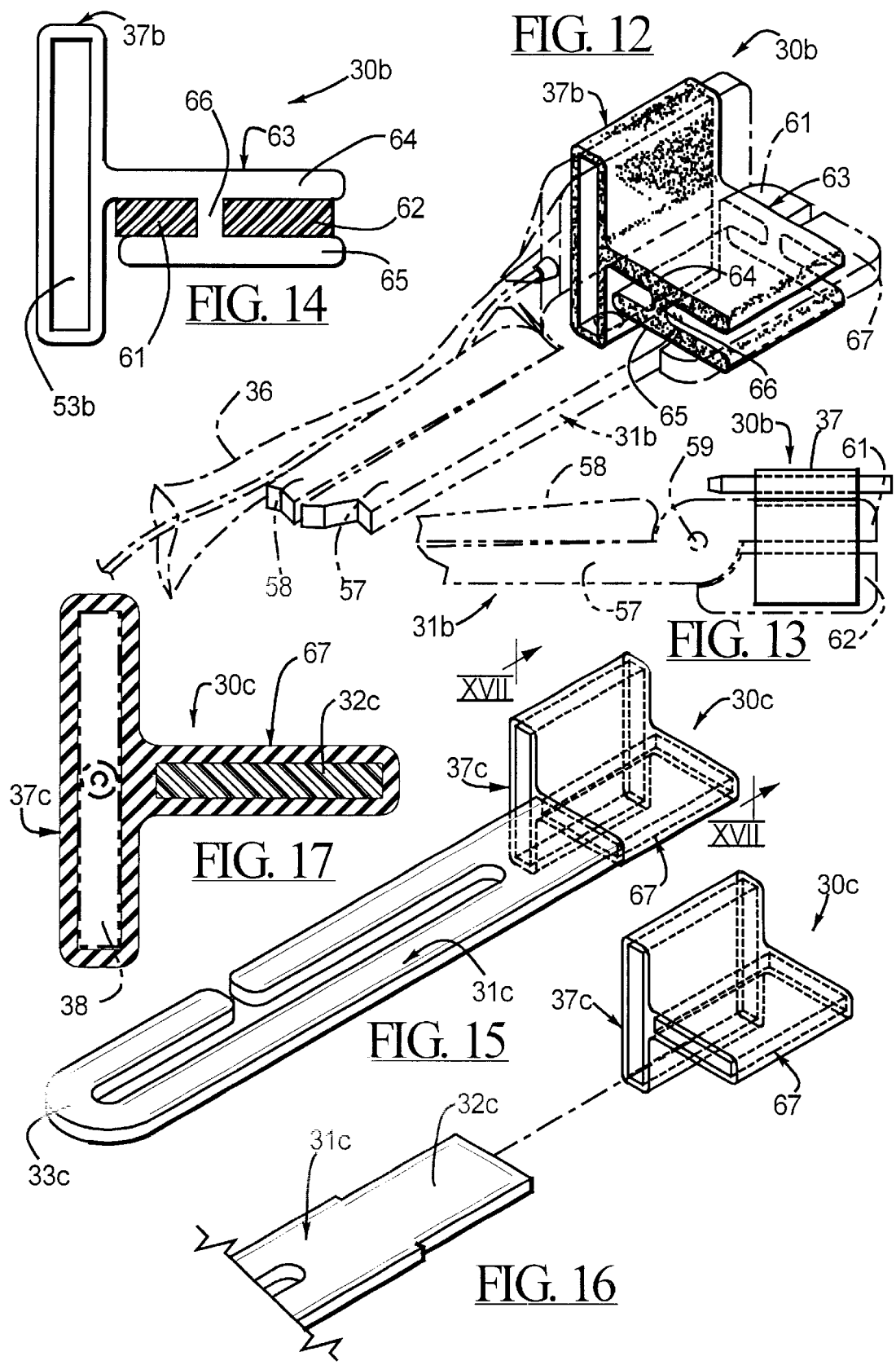

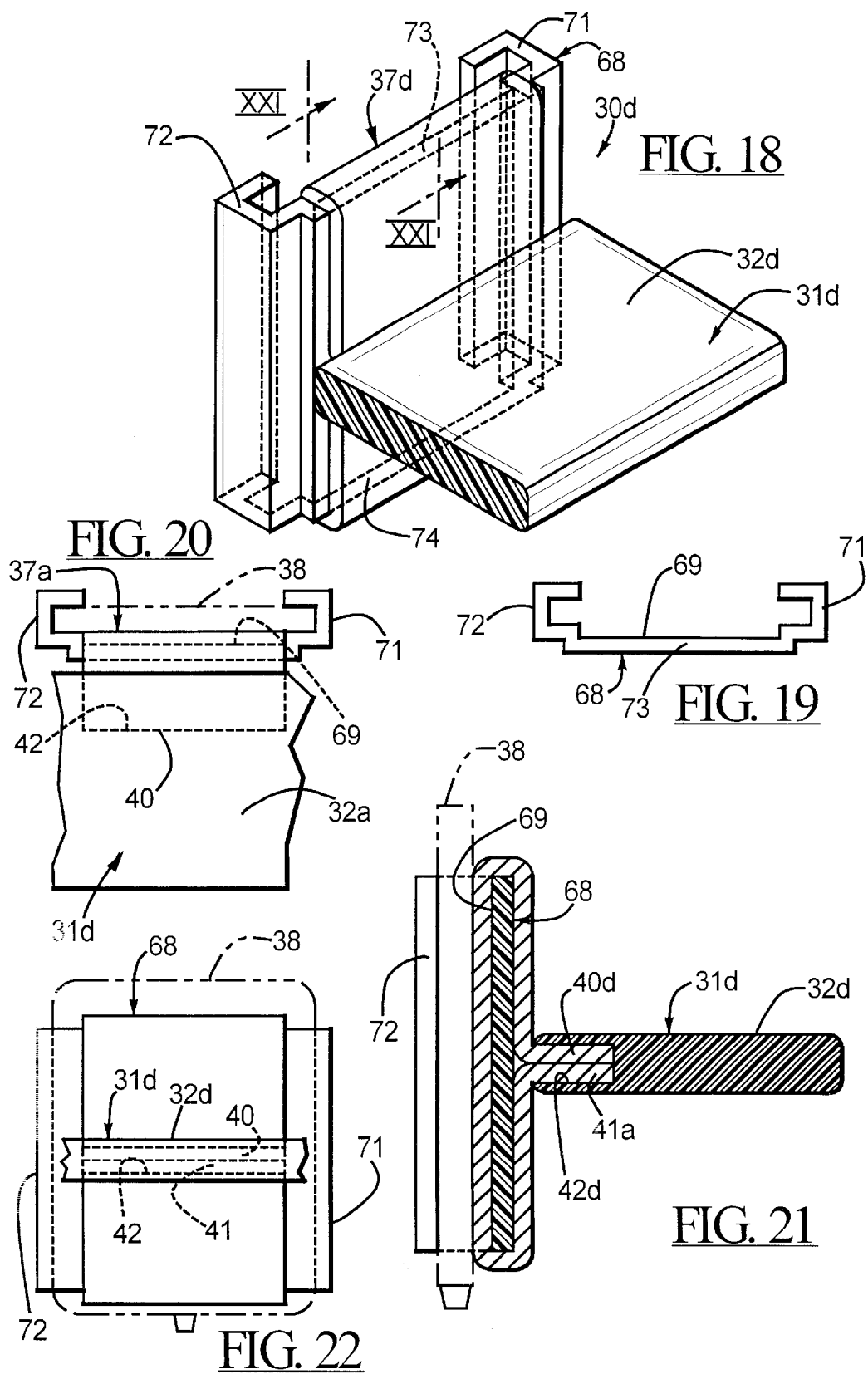

DENTAL X-RAY SENSOR HOLDER

FIELD OF THE INVENTION

The present invention relates generally to a holder for a dental X-ray image sensor. More specifically, the present invention relates to a device for holding a dental X-ray image detection device that is flexible and adaptable to the specific intraoral anatomy architecture of a patient's mouth.

BACKGROUND OF THE INVENTION

Holders for dental X-ray film packettes are known in the art. Two examples can be found in U.S. Pat. Nos. 5,256,982 and 4,075,494. The holders disclosed in these patents include a handle to assist the technician in correctly placing the film packette in the patient's mouth. However, for a variety of reasons, such X-ray film holders are cumbersome and uncomfortable for the patient. Bite-wing loops include a bite surface and a rigid paper-like flat loop for accommodating the X-ray packette.

Despite the longstanding popularity of bite-wing loops, there are many disadvantages with their use. For example, the lack of a handle makes them difficult for the technician to place in the mouth correctly. Further, the rigid connection between the X-ray film packette and the loop makes it difficult to adjust the position of the packette depending upon the patient's intraoral anatomy. Specifically, the architecture of patients' upper palate and base of the tongue will vary and the inability of the traditional bite-wing or rigid holding devices to accommodate for the variances between the architectures of individuals' upper palate and tongue area adversely affects the quality of the X-rays.

Further, and more important, the traditional X-ray film packettes are being replaced by digital X-ray sensors. Digital X-rays are quickly replacing traditional X-rays in the dental field because less radiation is used and images can be more quickly analyzed and manipulated using a computer.

However, problems have arisen with the use of digital X-ray sensors because they tend to be large and rigid, like traditional X-ray film packettes and, an accommodation must be made for the wire lead connected to the sensor. Still further, the inability of traditional bite-wing or traditional holding devices to accommodate for variations in the individual patient's intraoral anatomy is especially problematic with the use of digital X-ray sensors because of their size and rigidity.

Accordingly, there is a need for an improved holding device for digital X-ray sensors (also known as receptors and detectors) and traditional X-ray film packettes that overcomes the deficiencies of the prior art discussed above.

SUMMARY OF THE INVENTION

The aforenoted needs are satisfied by the present invention which provides a holder for a dental X-ray image sensor that comprises a handle having a first end. The first end of the handle is connected to a first elastic loop. The first elastic loop holds the dental X-ray image sensor. As a result of the combination of a handle and an elastic loop, the X-ray image sensor may be placed in the mouth and its position adjusted depending upon the individual patient's palate and the area lateral to the patient's tongue.

In an embodiment, the handle further comprises a second end that is connected to a second elastic loop. The second elastic loop can also hold a dental X-ray image sensor. In such an embodiment, the second elastic loop is arranged transversely in comparison to the first elastic loop.

In an embodiment, a portion of the handle spaced from the first end comprises a slot for accommodating an electrical lead.

In an embodiment, the handle is elongated and flat with an upper side and a lower side. The first elastic loop is formed from an elastic strip having a first end and a second end. The first end of the elastic strip is connected to the upper side of the handle while the second end of the elastic strip is being connected to the lower side of the handle thereby forming a loop that extends outward from an edge of the handle defined by the upper and lower sides of the handle.

In an embodiment, the handle is elongated and flat with an upper side and a lower side and a side edge disposed therebetween. The first end of the handle includes a horizontal slot disposed between the upper and lower sides and extending through the side edge. The first elastic loop is formed from an elastic strip having a first end and a second end. The first and second ends of the elastic loop are disposed in and secured in the horizontal slot of the handle to thereby fasten the loop to the handle.

In an embodiment, the elastic loop defines an opening that is parallel to the upper and lower sides of the handle.

In an embodiment, the first elastic loop defines an opening that is normal to the upper and lower sides of the handle.

In an embodiment with elastic loops disposed at both ends of the handle, one of the elastic loops defines an opening that is parallel to the upper and lower sides of the handle and the other elastic loop defines an opening that is normal to the upper and lower sides of the handle.

In an embodiment, the elastic loop is connected to a tail. The tail extends outward from the loop and has an I-beam shaped cross section with spaced-apart top and bottom members and a vertical member that connects the top and bottom members. The first end of the handle is split into two halves with the first half being received on one side of the vertical member and between the top and bottom members and the second half being received on an opposite side of the vertical member and between the top and bottom members.

In an embodiment, the holder further comprises a saddle which includes a back wall having two opposing ends. Each end of the back wall is connected to a bracket having a U-shaped configuration. The brackets being arranged in an opposing relationship to one another. The elastic loop extends around the back wall and between the U-shaped brackets to secure the saddle to the handle. The U-shaped brackets then accommodate a dental X-ray image sensor between the b rackets with the loop extending between the sensor and the back wall.

Other objects and advantages of the invention will become apparent upon reading the following detailed description and appended claims, and upon reference to the accompanying drawings.

BRIEF DESCRIPTION OF THE DRAWINGS

For a more complete understanding of the present invention reference should now be made to the accompanying drawings and detailed description as well as the appended claims. In the drawings:

FIG. 1 is a perspective view of a dental X-ray image sensor holder made in accordance with the present invention;

FIG. 2 is a perspective view of the holder shown in FIG. 1 accommodating an X-ray image sensor that is schematically linked to a computer;

FIG. 3 is another perspective view of the holder of FIG. 1 shown accommodating a sensor;

FIG. 4 is a sectional view taken substantially along lines 4—4 of FIG. 1;

FIG. 6 is a perspective view of another embodiment of a dental X-ray image sensor holder made in accordance with the present invention;

FIG. 7 is a plan view of the holder shown in FIG. 6;

FIG. 8 is a perspective view of the holder of FIG. 6 shown accommodating a sensor and wire lead;

FIG. 9 is a sectional view taken substantially along line 9—9 of FIG. 7;

FIG. 10 is a sectional view taken substantially along line 10—10 of FIG. 7;

FIG. 12 is a partial perspective view of another dental X-ray image sensor holder made in accordance with the present invention and also accommodating a sensor;

FIG. 13 is a partial plan view of the holder and sensor shown in FIG. 12;

FIG. 14 is a sectional view of the handle and loop portion of the holder of FIG. 12, without the sensor;

FIG. 15 is a perspective view of another embodiment of a dental X-ray image sensor holder made in accordance with the present invention;

FIG. 16 is a partial exploded view of the holder of FIG. 15;

FIG. 17 is a sectional view taken substantially along line 17—17 of FIG. 15;

FIG. 18 is a partial perspective view of yet another embodiment of a dental X-ray image sensor holder made in accordance with the present invention;

FIG. 19 is a top plan view of the saddle shown in FIG. 18;

FIG. 20 is a top plan view of the holder and saddle shown in FIG. 18;

FIG. 21 is a sectional view taken substantially along line 21—21 of FIG. 18; and FIG. 22 is a partial front plan view of the holder and saddle shown in FIG. 18.

Figure 5:
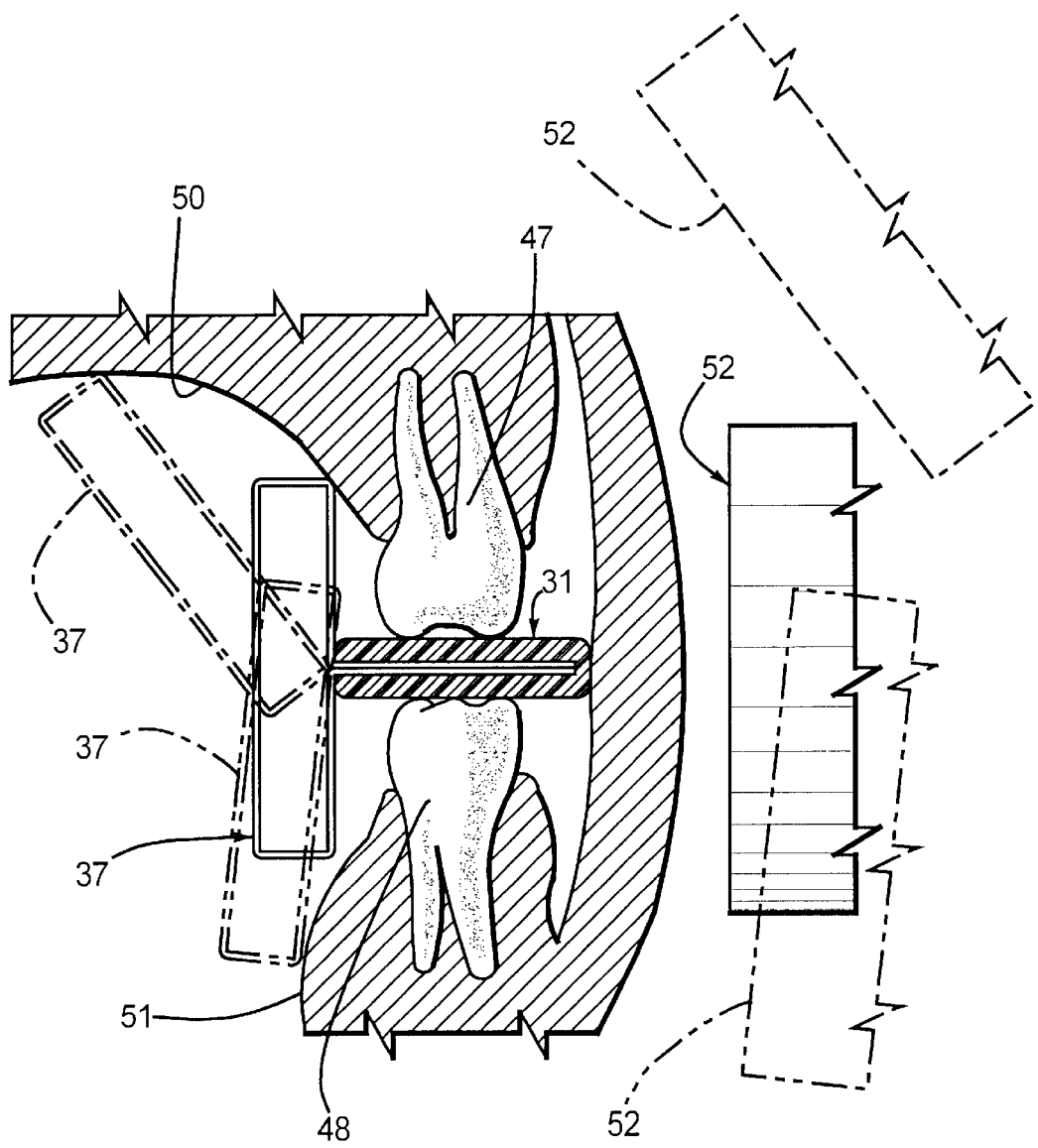
FIG. 5 is a side sectional view of the holder shown in FIG. 1 in place in a patient's mouth with various positions of the elastic loop being shown in phantom.
Figure 6A:
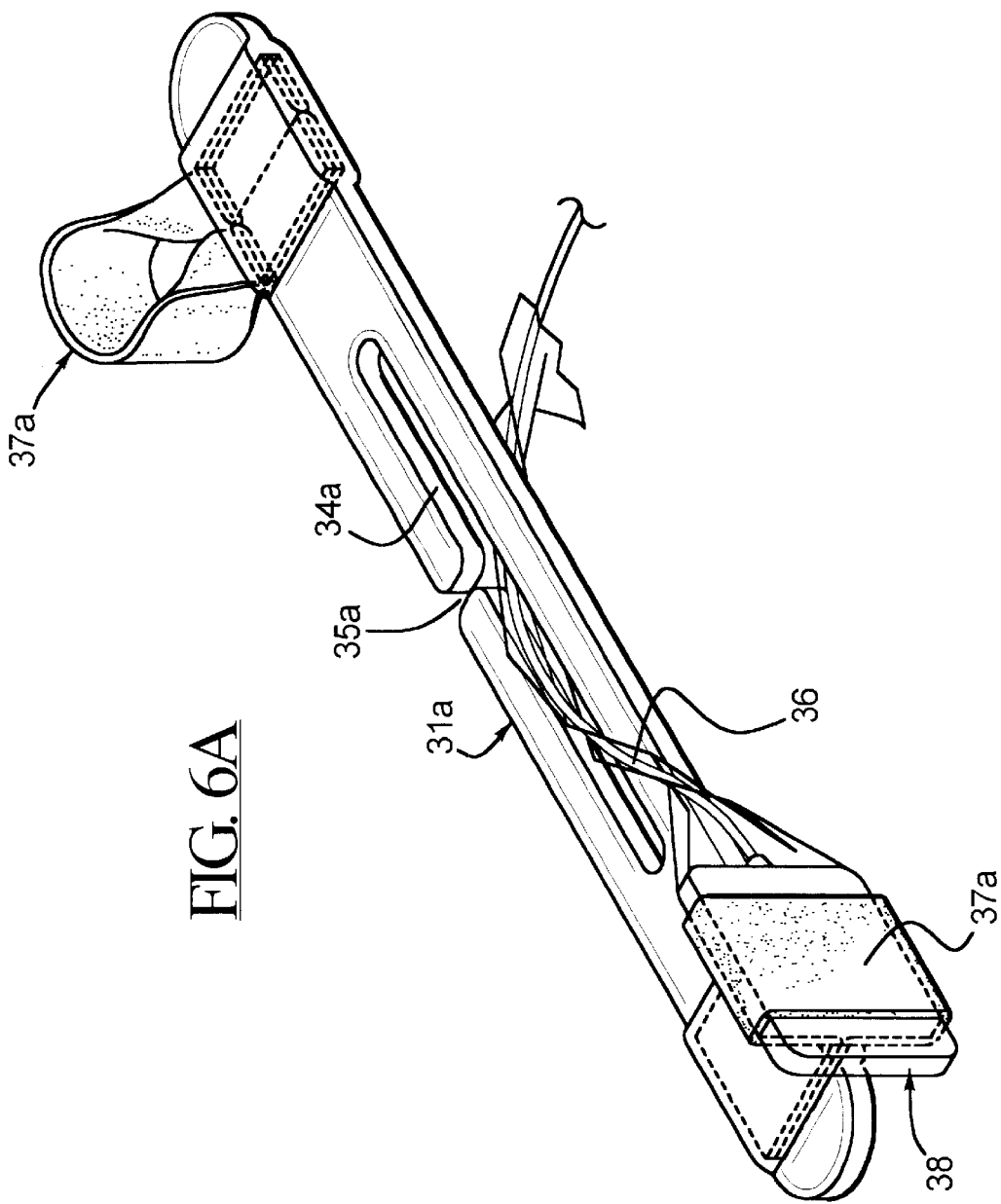
FIG. 6A is a perspective view of a dental x-ray sensor holder with a holder at both ends thereof.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

FIG. 1 illustrates one embodiment of the present invention in the form of a holder 30 that includes a flat elongated handle 31 having a first end 32 and a second end 33. Between the first end 32 and second end 33 is an elongated slot 34 having an access opening shown at 35. The slot 34 and access opening 35 are used to accommodate the wrapped wire lead shown at 36 in FIGS. 2 and 3.

Returning to FIG. 1, the first end 32 of the holder 30 is connected to a deformable or elastic loop 37. It will be understood that the use of "elastic" herein refers to any deformable and stretchable material that can be stretched to snugly accommodate a sensor 38 (see FIGS. 2 and 3) and that further allows the position of the sensor 38 to be adjusted with respect to the plane defined by the handle 31 of the holder 30. In the embodiment shown in FIGS. 1–4, the elastic loop 37 includes two free ends 40, 41 as best shown in the cross-sectional view of FIG. 4. The free ends 40, 41 of the loop 37 are accommodated in a slot 42 disposed towards the first end 32 of the handle 31. More specifically, the slot is disposed between the upper side 43 of the handle 31 and the lower side 44 of the handle 31 (see FIG. 4). Further, the slot extends through one side edge 45 (see FIG. 2). The free ends 40, 41 of the loop 37 can be secured in the slot 42 by a variety of means including glue, adhesive, fasteners or a molding process where the handle 31 is molded around the loop 37 and the partially molten material used to fabricate the handle seals the free ends 40, 41 of the loop 37 in the slot 42. Other means for securing the free ends 40, 41 in the slot will be apparent to those skilled in the art.

As shown in FIG. 2, the sensor 38 can be linked to a computer system 46.

FIG. 5 schematically illustrates the adjustability provided by use of the elastic loop 37 for holding a sensor 38. Specifically, the handle portion 31 is held in a horizontal position between a patient's upper teeth, one of which is shown at 47 and lower teeth, one of which is shown at 48. As illustrated in FIG. 5, the position of the loop 37 and sensor 38 (not shown in FIG. 5) can be adjusted due to the elasticity or deformability of the loop 37. Thus, the position of the sensor 38 can be adjusted to accommodate variation in a patient's palate 50 and base of tongue area 51. It will also be noted that the position of the X-ray tube head 52 may also need to be adjusted depending upon the position of the loop 37 and sensor 38.

Another embodiment of the present invention is illustrated in FIGS. 6–11. However, like reference numerals will be used to identify like or similar parts in the drawings. Specifically, referring to FIG. 6, it will be noted that the loop 37a is disposed in a position transverse to the loop 37 shown in FIGS. 1–5. Specifically, the opening 53a of the loop 37a extends transversely to a plane defined by the upper side 43a of the handle 31a. In contrast, referring to FIG. 1, it will be noted that the opening 53 extends parallel to a plane defined by the upper side 43 of the handle 31. The purpose of this transverse arrangement will be discussed in greater detail with respect to FIG. 11. As shown in FIG. 6A, loops 37a may be disposed at both ends of the handle 31a. The analogous arrangement could be fabricated for the embodiment shown in FIGS. 1–4.

Turning to FIGS. 7, 9 and 10, it will be noted that the free ends 40a, 41a are folded and accommodated in respective slots 42a and 42a'. As an alternative, a single slot could be provided. Again, the free ends 40a, 41a may be secured within the slots 42a, 42a' in a variety of means as discussed above with respect to the free ends 40, 41 of the embodiment illustrated in FIGS. 1–5.

Figure 11:
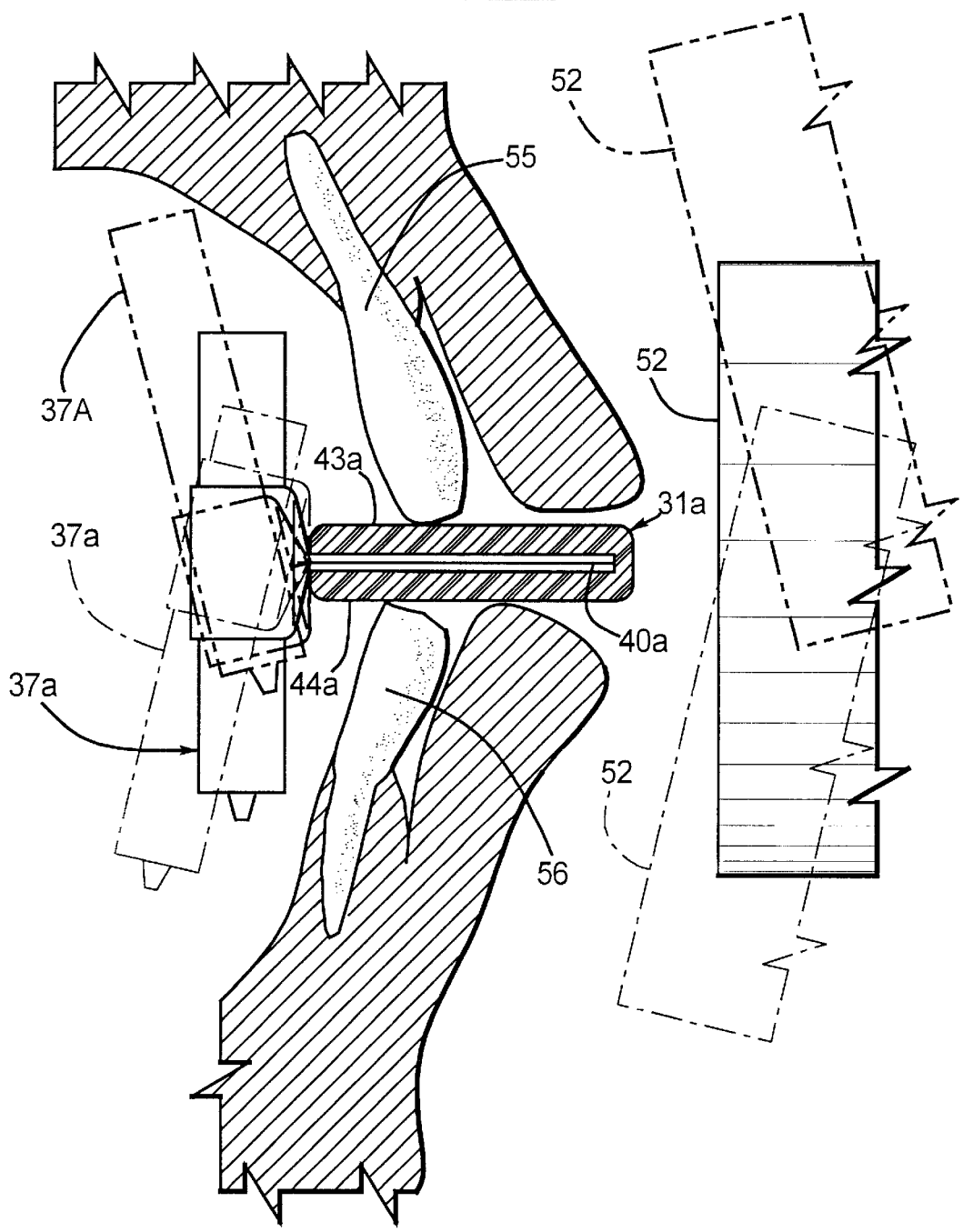
FIG. 11 is a side sectional view of the holder of FIG. 6 shown between the front teeth of a patient's mouth with various positions of the loop and sensor shown in phantom.

Turning to FIG. 11, the handle portion 31a is disposed between two front teeth including the upper tooth 55 and lower tooth 56. The adjustability of the loop 37a is illustrated. However, it will be noted that for the front teeth 55, 56, it is preferred to rotate the sensor 90° in comparison to the position used for the molars 47, 48. The rotation of the sensor is best seen when comparing FIGS. 8 and 2. By rotating the sensor 38 90°, the longer edges of the sensor are in alignment with the longer tooth structure of the front teeth 55, 56. Thus, a better view of the front teeth 55, 56 is provided.

Turning to FIGS. 12–13, yet another alternative embodiment of a holder 30b is illustrated. Specifically, referring to FIG. 12, the handle portion 31b is a hinged gripping device that includes a first half 57 pivotally connected to a second half 58 at a pin or rivet 59. The two halves 57, 58 each include a jaw member 61, 62 which is used to clamp the loop 37b in place. As shown in FIGS. 12 and 14, the loop 37b is connected to a tail 63. The tail 63 includes a top member 64, a bottom member 65 with a vertical member 66 extending therebetween. The vertical member 66 is disposed between the jaws 61, 62 of the halves 57, 58 respectively to hold the tail 63 and loop 37b in place. The loop 37b defines an elongated opening 53b for accommodating a sensor 38.

Yet another embodiment of the present invention is illustrated by way of the holder 30c shown in FIGS. 15–17. As shown in FIG. 16, the loop 37c is connected to a tail loop 67. The tail loop accommodates the tapered end 32c of the handle 31c. The loop 37c accommodates a sensor 38 as illustrated in FIG. 17.

Turning to FIGS. 18–22, yet another embodiment of the present invention is illustrated by way of the holder 30d. As best shown in FIGS. 18–20, the holder 30d includes an additional element in the form of a saddle 68. The saddle 68 includes a back wall 69 that is disposed between two U-shaped brackets 71, 72 that are arranged in an opposing relationship with respect to one another. As shown in FIG. 18, the saddle 68 is accommodated in the loop 37d so that the loop 37d extends over a top edge 73 of the saddle 68 and around a bottom edge 74 of the saddle 68. As shown in FIG. 20, the sensor 38 is accommodated between the U-shaped brackets 71, 72 of the saddle 68 and a portion of the loop 37d is disposed between the back wall 69 and the sensor 38. As shown in FIGS. 20–22, in a manner similar to the embodiment 30 illustrated in FIGS. 1–6, the loop 37d includes two free ends 4d, 41d that are accommodated in a slot 42d disposed in the end 32d of the handle portion 31d. It will be noted that the handle portion 31d is only partially shown in FIGS. 18–22.

Thus, a variety of dental X-ray image receptor, detector or sensor holders 30, 30a, 30c and 30d are illustrated and described. These holders enable the position of the sensors 38 to be manipulated in the mouth to provide correct positioning, improved images and improved patient comfort.

From the above description it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed is:

1. A holder for a dental X-ray image sensor comprising:
a handle comprising a first end, the first end of the handle being connected to a first elastic loop, the first elastic loop for holding the dental X-ray image sensor.

2. The holder of claim 1 wherein the handle comprises a second end, the second end being connected to a second elastic loop, the second elastic loop for holding the dental X-ray image sensor.

3. The holder of claim 1 wherein a portion of the handle spaced from the first end comprises a slot for accommodating an electrical lead.

4. The holder of claim 2 wherein a portion of the handle disposed between the first and second ends comprises a slot for accommodating an electrical lead.

5. The holder of claim 1 wherein the handle is elongated with an upper side and a lower side, the first elastic loop being formed from an elastic strip having a first end and a second end, the first end of the elastic strip being connected to the upper side of the handle, the second end of the elastic strip being connected to the lower side of the handle.

6. The holder of claim 1 wherein the handle is elongated with an upper side and a lower side with a side edge disposed therebetween, the first end of the handle comprising a horizontal slot disposed between the upper and lower sides and extending through the side edge, the first elastic loop being formed from an elastic strip having a first end and a second end, the first and second ends of the elastic loop being disposed in the horizontal slot of the handle.

7. The holder of claim 1 wherein the handle is elongated with an upper side and a lower side, and the first elastic loop comprises an opening that is parallel to the upper and lower sides of the handle.

8. The holder of claim 1 wherein the handle is elongated with an upper side and a lower side, and the first elastic loop comprises an opening that is normal to the upper and lower sides of the handle.

9. The holder of claim 2 wherein the first elastic loop comprises an opening that is parallel to the upper and lower sides of the handle and,
wherein the second elastic loop comprises an opening that is normal to the upper and lower sides of the handle.

10. The holder of claim 1 wherein the elastic loop is connected to a tail, the tail extending outward from the loop and having an I-beam shaped cross section with spaced-apart top and bottom members and a vertical member connecting top and bottom members, the first end of the handle comprising a first half and a second half, the first half being received on one side of the vertical member and between the top and bottom members, the second half being received on an opposite side of the vertical member and between the top and bottom members.

11. The holder of claim 1 further comprising a saddle comprising a back wall having two opposing ends and upper and lower edges, the upper edge being disposed between the two opposing ends and the lower edge being disposed between the two opposing ends, each end of the back wall being connected to a bracket having a U-shaped cross section, the brackets being arranged in an opposing relationship to one another, the elastic loop extending around the upper and lower edges and the back wall and between the brackets, the brackets accommodating the dental X-ray image sensor between the brackets with the loop extending between the sensor and the back wall.

12. A holder for a dental X-ray image sensor comprising:
a handle comprising a first end, the first end of the handle being connected to a first elastic loop, the first elastic loop for holding a saddle,
the saddle comprising a back wall having two opposing ends, each end of the back wall being connected to a bracket having a U-shaped cross section, the brackets being arranged in an opposing relationship to one another, the first elastic loop extending around the back wall and between the brackets, the brackets accommodating the dental X-ray image sensor between the brackets with the first elastic loop extending between the sensor and the back wall.

* * * * *